United States Patent [19]

Kawai et al.

[11] Patent Number: 4,980,151
[45] Date of Patent: Dec. 25, 1990

[54] ANTICARIOGENIC OR ANTIPERIODONTITIC AGENT

[75] Inventors: Yasuo Kawai, Atsugi; Kazuoki Ishihara, Tokyo, both of Japan

[73] Assignee: Kabushiki Kaisya Advance Kaihatsu Kenkyujo, Tokyo, Japan

[21] Appl. No.: 440,437

[22] Filed: Nov. 22, 1989

Related U.S. Application Data

[63] Continuation of Ser. No. 188,057, Apr. 26, 1988, abandoned, which is a continuation of Ser. No. 39,807, Apr. 15, 1987, abandoned, which is a continuation of Ser. No. 850,049, Apr. 10, 1986, abandoned.

[30] Foreign Application Priority Data

Apr. 12, 1985 [JP] Japan .................................. 60-76799

[51] Int. Cl.$^5$ ........................... A61K 7/16; A61K 7/26
[52] U.S. Cl. ......................................... 424/50; 424/49; 424/58; 514/835; 514/900
[58] Field of Search ..................................... 424/49–50, 424/58; 514/900, 835

[56] References Cited

U.S. PATENT DOCUMENTS 2,526,614 10/1950 Butterfield ............................ 424/50

FOREIGN PATENT DOCUMENTS 0127842 11/1978 Japan .

OTHER PUBLICATIONS

Scheibl, *Chem. Abst.,* 89, No. 12, 309 (1978), Abst. No. 95017k.
Pandya et al., *Chemical Abstracts,* 104, 303 (1986), Abst. No. 17601k.

*Primary Examiner*—F. T. Moezie
*Attorney, Agent, or Firm*—Finnegan, Henderson, Farabow, Garrett, Dunner

[57] ABSTRACT

An anticariogenic or antiperiodontitic agent containing, as an active component, yeast cells and/or water-soluble extracts of yeasts having antibacterial activity against *Streptococcus mutans* or *Bacteroides gingivalis.* This anticariogenic or antiperiodontitic agent has strong inhibitory effects on the growth of *Streptococcus mutans* causing dental caries and *Bacteroids gingivalis* causing periodontitis and has neither influence on intestinal microflora nor any side-effects when orally administered.

3 Claims, No Drawings

ANTICARIOGENIC OR ANTIPERIODONTITIC AGENT

This application is a continuation of application Ser. No. 07/188,057, filed Apr. 26, 1988, now abandoned which is a continuation of application Ser. No. 07/039,807, filed Apr. 15, 1987, now abandoned which is a continuation of application Ser. No. 06/850,049, filed Apr. 10, 1986 now abandoned.

BACKGROUND OF THE INVENTION

1. Field of the Invention

The present invention relates to anticariogenic or antiperiodontitic products such as beverages and foods which contain yeast cells and/or water soluble-extracts of yeasts which have an anticariogenic or antiperiodontitic activity.

2. Description of the Related Art

Several kinds of antibiotics and other substances acting in a manner similar to anti-bacterial substances against *Streptococcus mutans* and *Bacteroides gingivalis*, which are major pathogens of dental caries and periodontitis, respectively, have been proposed. However, their side-effects, for example, the influence of these substances on the intestinal microflora, are not yet fully understood, and accordingly, these substances are not used in practice, since there is no proof that they are safe for daily usage.

SUMMARY OF THE INVENTION

Accordingly, the objects of the present invention are to eliminate the above-mentioned possible side-effects of the prior art and to provide an anticariogenic or antiperiodontitic agent or composition having strong inhibitory effects on the growth of *Streptococcus mutans* causing dental caries and *Bacteroides gingivalis* causing periodontitis and having no influence on intestinal microflora when orally administered.

Other objects and advantages of the present invention will be apparent from the following description.

In accordance with the present invention, there is provided an anticariogenic or antiperiodontitic agent or composition containing, as an active component, yeast cells and/or water-soluble extracts of yeasts having antibacterial activity against *Streptococcus mutans* or *Bacteroides gingivalis*.

DESCRIPTION OF THE PREFERRED EMBODIMENT

The present inventors have found that yeast cells and/or their water-soluble extracts have strong inhibitory effects on the growth of *S.mutans* causing dental caries and *B.gingivalis* causing periodontitis, but show no toxicity in animal experiments and no influence on intestinal microflora when orally administered, since they are originally ingredients of foods.

The types and bacteriological characteristics, the preparation of the anticariogenic or antiperiodontitic products, the anti-bacterial activity, the forms in practical use, and the like of yeasts and water-soluble extracts according to the present invention will now be described in detail hereinbelow.

Yeasts

Various kinds of yeasts belonging to the genus Saccharomyces, Kluyveromyces, Torulopsis, Torulospora, Schizosaccharomyces, and especially for safety, such yeasts used for fermented foods and beverages as baker's yeasts, brewer's yeasts, sake-yeasts, compressed yeasts, and the like, are exemplified for the preparation of the bacterial cell products according to the present invention.

That is, *Saccharomyces cerevisiae*, *S.ellipsoideus*, *S.globosus*, *S.chevalieri*, *S.microellipsodes*, *S.exiguus*, *S.heterogenicus*, *S.acidifaciens* (*baillii*), *S.fragilis* (*Kluyveromyces fragilis*), *S.carlsbergensis*, *S.rouxii*, *S.uvarum*, *S.bisporus*, *Torulopsis versatilis*, *Torulospora microellipsodes*, *Schizosaccharomyces pombe*, and the like can be shown. These yeasts have been commercialized; for example, dried yeast "Fukkura ®" from Nippon Seifun Co., Ltd., "Super Kameriya ®" from Nisshin Seifun Co., Ltd., and the like are available on the market, and these yeasts have been deposited at the American Type Culture Collection as standard strains. Accordingly these yeasts are easily available.

Several examples of such standard strains of the American Type Culture Collection are : *S.cerevisiae* ATCC 287, *S.chevalieri* ATCC 9804, *S.exiguus* ATCC 10599, *S.heterogenicus* ATCC 10601, *S.acidifaciens* ATCC 8766, *S.fragilis* ATCC 8554, *S.carlsbergensis* ATCC 18976, *S.rouxii* ATCC 2623, *S.uvarum* ATCC 24966, *S.bisporus* ATCC 2607, *Torulopsis versatilis* ATCC 20191, *Torulospora microellipsodes* ATCC 10605, and *Schizosaccharomyces pombe* ATCC 16979.

The microbiological characteristics of the above-exemplified strains according to the present invention correspond to those described in the following articles:

(1) "Laboratory Manual of Agricultural Chemistry"Revised ed. vol.2: 816–841 (1980) Sangyo Tosho Publishing Co., Ltd. (in Japanese)

-2) "Methods in Agricultural Chemistry"3rd ed. vol. II: 256–263 (1980) Asakura Publishing Co., Ltd. (in Japanese)

Any conventional cultivation methods can be applied to cultivation of the above-exemplified strains according to the present invention; for example, those microorganisms can be cultivated in a medium (pH 6.0) containing 2% peptone, 2% glucose, and 1% yeast extract, or in a potato-glucose medium shown below, and the like, under an aerobical condition at 30° C. to 40° C. for several hours to several days.

Preparation of anticariogenic and antiperiodontitic products

The living cells, the dead cells having undergone various treatments, and the water-soluble extracts of the yeasts used in the present invention and suitable for use as anticariogenic and antiperiodontitic agents, are typically prepared as follows:

1. Hot-water extraction

The harvested becterial cells were suspended in water, and were heated at 80° C. to 130° C., preferably at 100° C. to 125° C., for several minutes to several hours. The water-soluble anticariogenically and antiperiodontitically active extracts were obtained by centrifugation, etc., to remove the water-insoluble solids.

Physiological saline (0.85% NaCl, etc.), various kinds of pH-adjusted buffers, various kinds of salt solutions, water/alcohol (methanol, ethanol, etc.) $> \frac{1}{2}$ (w/w), and various aqueous solvents can be also used for the extraction. Moreover, the whole cell preparations heat-treated in hot-water as described above can be also used for suitable anticariogenic and antiperiodontitic agents of the present invention, as powder or other preparation forms, by lyophilization, drying in vacuo, and spray drying.

2. Sterilization

The cell preparations made by spray-drying or heat-treatment with other methods or sonication (for example, at 15 KC for 1 hour) can be also used for useful anticariogenic and antiperiodontitic agents of the present invention, and the water-soluble components of the sterilized cell preparations as shown above can be also used for anticariogenically and antiperiodontitically active fractions in the present invention.

Physiological characteristics

1. Antibacterial activity

As shown in the examples, the anticariogenic and antiperiodontitic products of the present invention effectively depress or inhibit the growth of S.mutans which causes dental caries and B.gingivalis which causes periodontitis.

2. Toxicity

The anti-bacterial products according to the present invention are originally ingredients of foods and are substantially nontoxic upon oral administration.

Forms in practical use

The anticariogenic and antiperiodontitic products of the present invention can be practically used in the form of, for example, tooth-paste, gargles, troches, chewing gum, and the like, and in the form of various kinds of anticariogenically and antiperiodontitically depressive and preventive foods and beverages added with the anticariogenic and antiperiodontitic products. The amount used in practical use is about 0.001% to 1% by weight, based on the total weight of the composition.

EXAMPLES

The present invention will now be further shown by, but is no means limited to, the following examples.

1. Preparation of the hot water-soluble extract

An yeast (S.cerevisiae ATCC 287) was incubated with agitation in a potato-glucose medium at 35° C. for 48 hours. After centrifugation of the culture, the yeast cells were washed in physiological saline or water, and harvested by centrifugation, and this process was carried out twice. The harvested cells were heat-treated at 110° C. to 121° C. for 5 to 15 minutes, and dried by lyophilization or heat-drying at an environmental temperature of 60° C. to 130° C. to obtain the heat-dried cells of the yeast. The dried cells were then suspended in a 20-fold volume of water, and were heated at 80° C. for 5 minutes, and the supernatant was collected by centrifugation. The supernatant was lyophilized or heat-dried to obtain the hot water-soluble extracts in which the yield was about 30% by weight of the dried cells.

Composition of potato-glucose medium

| Potato-extract | 20% |
| Glucose | 2% |
| Methionine | 0.3% | pH 6.8, sterilized at 121° C. for 15 minutes.
The potato extract is obtained from potatoes by heat-treatment at 110° C. for 10 minutes and lyophilization.

2. Growth inhibition of S.mutans

The sterile solution of the hot water-soluble extracts mentioned above (the extracts were dissolved in water, the pH adjusted to 7, and sterilization done by autoclaving at 121° C. for 15 minutes or filtration with membrane filters) were added into the sterile Todd-Hewitt broth medium together with sterile distilled water to adjust the concentration of the medium to one half and to adjust the concentration of the hot water-soluble extracts. To this medium, S.mutans 8148 (supplied from the National Institute of Health, Japan) was inoculated at the viable cell concentration of $10^6$/ml. The viable cell number was enumerated periodically, for 0 to 24 hours after inoculation. In the controls, a 0.85% NaCl solution was added instead of the extracts.

Composition of Todd-Hewitt broth medium

Dissolve 30 grams/liter distilled water of powder containing the following formula.

| Ingredient | Parts by weight |
| --- | --- |
| Infusion from beef heart | 500 |
| Peptone | 20 |
| Dextrose | 2 |
| NaCl | 2 |
| $Na_2HPO_4$ | 0.4 |
| $Na_2CO_3$ | 2.5 |
| pH 7.8 | |

Autoclaved at 121° C. for 15 minutes.
(Updyke et al., Appl. Microbiol., 2: 177 (1954))
The result is shown in Table 1.

TABLE 1

| Concentration of hot water-soluble extracts (%) | Viable cell number (log/ml) | |
| --- | --- | --- |
| | 12 hours after | 24 hours after |
| 0.015 | 7.7 | 8.5 |
| 0.03 | 7.5 | 8.1 |
| 0.05 | 7.0 | 7.2 |
| 0.1 | 6.6 | 6.5 |
| 0.2 | 6.5 | 6.3 |
| Control | 7.9 | 8.9 |

3. Growth inhibition of B.gingivalis

A GAM broth medium containing hot water-soluble extracts obtained by the preparation method described in Example 1 was inoculated with B.gingivalis AD 50001, which was isolated from a human oral cavity, at a concentration of $10^7$/ml under an anaerobic condition, and was incubated. The viable cell number (log/ml) was enumerated periodically, for 48 hours after inoculation. In the controls, a 0.85% NaCl solution was added instead of the extracts. The result is shown in Table 2.

TABLE 2

| Concentration of hot water-soluble extracts (%) | Viable cell number (log/ml) | |
| --- | --- | --- |
| | 24 hours after | 48 hours after |
| 0.03 | 7.4 | 8.1 |
| 0.07 | 6.6 | 4.6 |
| 0.15 | 4.9 | 3.3 |
| Control | 8.6 | 9.5 |

Composition of GAM broth medium

| GAM broth (Nissui Pharmaceutical Co., Ltd.) code 05422 | |
| --- | --- |
| | 59.0 g |
| Peptone | 10.0 g |
| Soybean peptone | 3.0 g |
| Proteose peptone | 10.3 g |
| Digested serum powder | 13.5 g |
| Yeast extract | 5.0 g |
| Meat extract | 2.2 g |
| Liver extract powder | 1.2 g |
| Glucose | 3.0 g |
| $KH_2PO_4$ | 2.5 g |
| NaCl | 3.0 g |
| Soluble starch | 5.0 g |
| L-Cysteine hydrochloride | 0.3 g |
| Sodium thioglycollate | 0.3 g |
| Distilled water | to 1 liter |

4. Antibacterial activity of other yeasts

The inhibitory effect of *Torulopsis versatilis* ATCC 20191, *Torulospora microellipsodes* ATCC 10605, and *Schizosaccharomyces pombe* ATCC 16979, which are commercially available, on the growth of *S.mutans* and *B.gingivalis* was examined and the results are shown as summarized in Tables 3 and 4, respectively. The concentration of the hot water-soluble extracts of the yeasts was 0.2% and 0.15% against *S.mutans* and *B.gingivalis*, respectively.

Although the main pharmacological actions are observed with the hot water-soluble extracts, the heat-treated cells can be used practically as the antibacterial agent.

TABLE 3

| Strains | Viable cell number (log/ml) | |
| --- | --- | --- |
| | 12 hours after | 24 hours after |
| *Torulopsis versatilis* ATCC 20191 | 6.5 | 6.3 |
| *Torulspora microellipsodes* ATCC 10605 | 6.6 | 6.3 |
| *Schizosaccharomyces pombe* ATCC 16979 | 6.5 | 6.4 |
| Control | 7.8 | 9.0 |

TABLE 4

| Strains | Viable cell number (log/ml) | |
| --- | --- | --- |
| | 24 hours after | 48 hours after |
| *Torulopsis versatilis* ATCC 20191 | 4.9 | 3.1 |
| *Torulospora microellipsodes* ATCC 10605 | 5.1 | 3.5 |
| *Schizosaccharomyces pombe* ATCC 16979 | 3.6 | |
| Control | 8.5 | 9.5 |

5. Acute toxicity

The hot water-soluble extracts prepared according to the above-mentioned preparation methods were intraperitoneally administered into ICR mice (6 week-old, male, average body weight of 31.0±0.6 g) in the form of an 0.5 ml saline solution containing the extracts corresponding to $9\times10^9$, $9\times10^8$, or $9\times10^7$ yeast cells/mouse (10 mice in each group). The thanatobiological observation of the mice was carried out for 14 days.

The $LD_{50}$ values (mg/mouse) calculated according to the Behrens-Kärber method were more than 7.3 mg/mouse in any case. Both of the yeast cells and the hot water-soluble extracts of the present invention were substantially nontoxic in the case of daily oral administration.

Examples in practical use

1. Tooth-paste

| | Wt. % |
| --- | --- |
| Secondary calcium phosphate | 30–50 |
| Glycerin | 15–20 |
| Carrageenan | 0.5–20 |
| Sodium lauryl sulfate | 0.8–1.5 |
| p-Oxybutyl benzoate | 0.001–0.005 |
| Flavor | 0.5–1.5 |
| Heat-treated dead cells | 0.1–10 |
| (autoclaved at 121° C. for 25 minutes) of the present invention | |
| | 100 |

2. Gargles

| | Wt. % |
| --- | --- |
| Ethanol (90%) | 15–20 |
| Saccharin | 0.1–0.5 |
| Sodium acyltaurate | 0.2–0.6 |
| Gelatin | 0.1–0.6 |
| Flavor | 0.5–1.5 |
| Chlorohexidine | 0.002–0.007 |
| Hot water-soluble extracts (autoclaved at 121° C. for 25 minutes) of the present invention | 1.0–12 |
| Water | Remainder |
| | 100 |

3. Chewing gum

| | Wt. % |
| --- | --- |
| Gum base | 18–25 |
| $CaCO_3$ | 1–5 |
| Saccharin | 0.05–0.2 |
| Lactose | 65–75 |
| Heat-treated dead cells | 0.5–8 |
| (Autoclaved at 121° C. for 25 minutes) of the present invention | |
| | 100 |

4. Anticariogenic or antiperiodontitic foods and beverages

The heat-treated dead cells or the hot water-soluble extracts of the present invention can be used for anticariogenic or antiperiodontitic foods and beverages by addition of 0.001 to 10% (dry weight) of the preparation into bread, cookies, candies, yogurt, fruit juice, tea, coffee, etc., and other general foods and beverages.

We claim:

1. An anticariogenic or antiperiodontitic composition comprising an anticariogenically or antiperiodontitically effective amount of water-soluable extracts of yeasts belonging to the genus Saccharomyces, Kluyveromyces, Torulopsis, Torulospora, or Schizosaccharomyces prepared by heating the cells of yeast at a temperature of 80° C. to 130° C. in an aqueous solvent and having anti-bacterial activity against *streptococcus mutans* or *Bacteriodes gingivalis*, and an orally acceptable carrier.

2. The composition of calim 1, wherein the yeast is at least one member selected from the group consisting of baker's yeast, brewer's yeast, sake-yeasts, and compressed yeasts.

3. The composition of claim 1, wherein the yeast belongs to *Saccharomyces cerevisiae, S.ellipsoideus, S.globosus, S.chevalieri, S.microellipsodes, S.exiguus, S.heterogenicus, S.acidifaciens, S.fragilis, S.carlsbergensis, S.rouxii, S.uvarum, S.bisporus, Torulopsis versatilus, Torulospora microellipsodes,* or *Schizosaccaromyces pombe.*

* * * * *

UNITED STATES PATENT AND TRADEMARK OFFICE
CERTIFICATE OF CORRECTION

PATENT NO. : 4,980,151

DATED : December 25, 1990

INVENTOR(S) : Yasuo Kawai and Kazuoki Ishihara

It is certified that error appears in the above-identified patent and that said Letters Patent is hereby corrected as shown below:

Abstract, line 7, change "Bacteroids" to --Bacteroides--;

Col. 6, Claim 1, line 61, change "water-soluable" to --water-soluble--; and line 66, change "streptococcus" to --Streptococcus--;

Col. 7, Claim 2, line 1, change "calim" to --claim--.

Col. 8, Claim 3, line 4, change "Schizosaccaromyces" to --Schizosaccharomyces--.

Signed and Sealed this

Thirteenth Day of October, 1992

Attest:

DOUGLAS B. COMER

*Attesting Officer*   *Acting Commissioner of Patents and Trademarks*